US009814730B2

(12) United States Patent
May

(10) Patent No.: US 9,814,730 B2
(45) Date of Patent: *Nov. 14, 2017

(54) PHARMACEUTICAL COMPOSITION OR GROUP OF COMPOSITIONS FOR INHIBITING AUTOCRINE HCG PRODUCTION IN ADULT HUMAN CELLS

(71) Applicant: FLAMINA HOLDING AG, Zug (CH)

(72) Inventor: Michael May, Zug (CH)

(73) Assignee: FLAMINA HOLDING AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/422,844

(22) Filed: Feb. 2, 2017

(65) Prior Publication Data
US 2017/0143739 A1 May 25, 2017

Related U.S. Application Data

(63) Continuation of application No. 14/531,435, filed on Nov. 3, 2014, now Pat. No. 9,603,856.

(30) Foreign Application Priority Data

Nov. 3, 2013 (EP) .................................... 13191319
Nov. 3, 2013 (EP) .................................... 13191320
May 15, 2014 (EP) .................................... 14168550

(51) Int. Cl.
*A61K 31/567* (2006.01)
*A61K 9/00* (2006.01)

(52) U.S. Cl.
CPC ............ *A61K 31/567* (2013.01); *A61K 9/006* (2013.01); *A61K 9/0014* (2013.01); *A61K 9/0019* (2013.01)

(58) Field of Classification Search
IPC .............................. A61K 31/567,9/0019, 9/006
See application file for complete search history.

(56) References Cited

U.S. PATENT DOCUMENTS

| 5,622,943 | A | 4/1997 | Hodgen |
| 6,043,234 | A | 3/2000 | Stockemann et al. |
| 6,316,432 | B1 | 11/2001 | Schwede et al. |
| 6,608,074 | B2 | 8/2003 | Chwalisz et al. |
| 2004/0102422 | A1 | 5/2004 | Gaston |
| 2008/0261929 | A1 | 10/2008 | Hoffmann et al. |
| 2013/0131030 | A1 | 5/2013 | Belanoff et al. |

FOREIGN PATENT DOCUMENTS

| CA | 2195425 C | 3/2008 |
| EP | 2210585 A1 | 7/2010 |
| WO | 9317686 A1 | 9/1993 |
| WO | WO 2009/134725 | * 11/2009 |

OTHER PUBLICATIONS

Yuan et al., "The Chemopreventive Effect of Mifepristone on Mammary Tumorigenesis is Associated With an Anti-Invasive and Anti-Inflammatory Gene Signature," Cancer Prev Res, vol. 5, No. 5, pp. 754-764, 2012.
Lanari et al., "Antiprogestins in Breast Cancer Treatment: Are We Ready?". Endocrine-Related Cancer, vol. 19, pp. R35-R50, 2012.
Guil-Luna et al., "Aglepristone Decreases Proliferation in Progesterone Receptor-Positive Canine Mammary Carcinomas". J Vet Intern Med, vol. 25, pp. 518-523, 2011.
Jan. 23, 2015 European Search Report issued in European Application No. 14191419.2.
Santucci-Pereira et al., "Mimicking Pregancy as a Strategy for Breast Cancer Prevention". Breast Cancer Manag., vol. 2, No. 4, pp. 283-294, 2013.
Aug. 9, 2016 Office Action Issued in U.S. Appl. No. 14/531,435.
Tsampalas et al., "Human Chorionic Gonadotropin: A Hormone With Immunological and Angiogenic Properties". Journal of Reproductive Immunology., pp. 1-6, 2010.
Maria et al., "Termination of Early Pregancy by a Single Dose of Mifepristone (Ru 486), a Progesterone Antagonist". European Journal of Obstetrics and Reproductive Biology, vol. 28, pp. 249-255, 1988.
Wu et al., "Effects of Mifeprisone on the Proliferation, Apoptosis, and Taxol Sensitivity of Drug-Resistant Human Ovarian Cancer Cells". XP002728256, http://en.cnki.com.cn'Article_en/ CJFDTOTAL-ZGAZ201202009.htm, 2012.
Tieszen et al., "Antiprogestin Mifepristone Inhibits the Growth of Cancer Cells of Reproductive and Non-Reproductive Origin Regardless of Progesterone Receptor Expression". BMC Cancer, vol. 11, No. 1, p. 287, 2011.
Navo et al., "In Vitro Evaluation of the Growth Inhibition and Apaptosis Effect of Mifepristone (Ru 486) in Human Ishikawa and HEC1A Endometrial Cancer Cells Lines". Cancer Chemother Pharmacol, vol. 62, pp. 483-489, 2008.
Aranda et al., "Nuclear Hormone Receptor and Gene Expression". Physiological Reviews, vol. 8, No. 3, pp. 1269-1304, 2001.
Yuill, "Cellular Adaptation to Toxicity". National Library of Medicine, 2006.
Cole, "HCG, the Wonder of Today's Science". Reproductive Biology and Endocrinology, http://www.rbej.com/content/10/1/27, 2012.
Fieni et al., "Mid-Pregnancy Termination in Bitches With an Antiprogestin: Aglepristone (Ru 534)". Laboratory of Biotechnology and Pathology of Reproduction, National Veterinary School, Advances in Dog, Car, and Exotic Carnivore Reproduction, p. 111, 2000.

(Continued)

*Primary Examiner* — Shirley V Gembeh
(74) *Attorney, Agent, or Firm* — Oliff PLC

(57) ABSTRACT

A pharmaceutical composition for use as medicament that inhibits autocrine Human Chorionic Gonadotropin (HCG) production and thus carcinogenesis in adult human cells, the composition comprising at least a first pharmaceutically acceptable carrier and an active agent that is a competitively binding progesterone antagonist binding to steroid receptors of human cells, wherein the composition is provided in units designed for the monthly, semi-annual or annual application of the active agent in annual dosages in the range between 0.1 mg to 10.0 mg per kg of person/body-weight.

28 Claims, No Drawings

(56) References Cited

OTHER PUBLICATIONS

Duffy et al., "Guideliness for the Use of Tumour Markers". The Associate of Biochemists in Ireland, 4th Edition, pp. 1-27, 2010.
New Zealand Data Sheet of Mifegyne, XP855181287, Jul. 3, 2013.

* cited by examiner

PHARMACEUTICAL COMPOSITION OR GROUP OF COMPOSITIONS FOR INHIBITING AUTOCRINE HCG PRODUCTION IN ADULT HUMAN CELLS

This is a Continuation of application Ser. No. 14/531,435 filed Nov. 3, 2014. The disclosure of the prior application is hereby incorporated by reference herein in its entirety.

The present invention relates to a pharmaceutical composition or a group of pharmaceutical compositions for inhibiting autocrine production of HCG (Human Chorionic Gonadotropin) in cells of adult human organisms. More particularly the present invention relates to a pharmaceutical composition or a group of pharmaceutical compositions for inhibiting carcinogenesis that is caused by autocrine HCG production.

BACKGROUND OF THE INVENTION

Based on growth and aging of the U.S. population, medical expenditures for cancer in the year 2020 are projected to reach at least $158 billion. If newly developed tools for cancer diagnosis, treatment, and follow-up continue to be more expensive, medical expenditures for cancer could reach as high as $207 billion, said the researchers from the National Cancer Institute (NCI), part of the NIH (see http://www.nih.gov/news/health/jan2011/nci-12.htm).

Budget for cancer research projects of the National Cancer Institute (NCI) is in the range of USD 5 billion (see http://www.cancer.gov). A multiple of this amount is invested in cancer research worldwide by national institutes and pharmaceutical companies. The research projects funded relate primarily to the treatment of cancer, which often leads to prolonged life but not recovery.

Besides treatment, early detection of cancer is also a topic of science (see http://www.who.int/cancer/detection/en/).

Research into cancer prevention and cancer causes is primarily dedicated to the investigation of external influences to the human body, such as influences of nutrition and beverages, influence of smoking and environmental influences.

A widely neglected field remains research and investigation of prevention and causes of cancer that have no external basis, but an internal basis to which the present invention is related.

According to [1], Marie Tsampalas et al., "Human chorionic gonadotropin: A hormone with immunological and angiogenic properties", 2010 Elsevier Ireland Ltd., the mechanisms underlying human implantation and particularly immune tolerance of pregnancy still remain to be defined in detail. HCG is the prime mediator by which the embryo announces its presence to the maternal organism since it is produced even before implantation. Among the wide range of mediators present at the implantation site, a role is becoming evident for HCG as specific blastocyst signal involved in orchestrating the implantation cascade. HCG is implicated in several actions that promote immune tolerance and angiogenesis and thus has physiological important implications for successful pregnancy. HCG is one of the earliest molecules produced by the embryo. Indeed, its mRNA is transcribed as early as the 8-cell stage and the blastocyst produces the protein before its implantation. HCG is increasingly produced after implantation by the syncitiotrophoblast. Significant levels of HCG can already be measured in the maternal blood 10 days after conception. The peak of HCG production is reached between the 10th and the 11th week of gestation, then the production decreases at the 12th week to remain at low levels for the remainder of pregnancy. HCG affects the corpus luteum to prevent luteolysis and favour stimulation of progesterone production.

HCG production is stimulated by the producing cell itself, it is known as autocrine hormone production that takes place during the above described embryonic phase. This process of autocrine hormone secretion by embryonic cells is stopped before parturition. From then on, all hormone production is controlled by brain activity. After the specified initial time period HCG is no longer produced in genetically healthy adult human cells.

By determination, the descendants of the totipotent zygote successively lose their totipotenz and follow their predetermined determination. Remarkably, each healthy cell has a cell-memory, retaining its own cell proliferation, a necessity for organized tissues, organs and stably differentiated cell types.

The presence of HCG in the human body can be measured. Pregnancy testing for example is based on the measurement of the concentration of HCG contained in the maternal urine.

HCG interacts with the Lutheneizing hormone (LH) receptor of the mother and promotes the maintenance of the corpus luteum during the beginning of pregnancy. This allows the corpus luteum to secrete the hormone progesterone, which enriches the uterus with blood vessels and capillaries so that it can sustain the growing foetus. The application of competitively binding progesterone antagonists induces an abortion, since they occupy the receptor of the progesterone controlling gene that functions to maintain pregnancy.

As described in [2], B. Maria et al., "Termination of early pregnancy by a single dose of mifepristone (RU486), a progesterone antagonist", European Journal of Obstetrics & Gynecology and Reproductive Biology, vol. 28, no. 3, pages 249-255, (Jul. 1, 1988), the compound RU486, also known as Mifepristone, is an important progestin antagonist that effectively and safely terminates early pregnancy, when used in conjunction with a prostaglandin.

Derivatives or descendants of RU486 are described in [3], U.S. Pat. No. 6,608,074B2 and [4], U.S. Pat. No. 6,316,432B1.

As described in [5], "New Zealand Data Sheet of Mifegyne", 3 Jul. 2013, XP855181287, Mifepristone is commercially available in tablets of 200 mg under the trade name Mifegyne®. Mifepristone is a synthetic steroid with an antiprogestational action as a result of competition with progesterone at the progesterone receptors. As further described, doses higher or equal to 1 mg/kg, mifepristone antagonises the endometrial and myometrial effects of progesterone.

[6], Wu et al: "Effects of mifepristone on the proliferation, apoptosis, and taxol sensitivity of drug-resistant human ovarian cancer cells", 2012, XP002728256, http://en.cnki.com.cn/Article en/CJFDTOTAL-ZGAZ201202009.htm,

[7], CHELSEA R TIESZEN ET AL: "Antiprogestin mifepristone inhibits the growth of cancer cells of reproductive and non-reproductive origin regardless of progesterone receptor expression", BMC CANCER, BIOMED CENTRAL, LONDON, vol. 11, no. 1, 27 May 2011, page 287, XP021099346, ISSN: 1471-2487, DOI: 10.1186/1471-2407-11-207, and

[8], MARISA A NAVO ET AL: "In vitro evaluation of the growth inhibition and apoptosis effect of mifepristone (RU486) in human Ishikawa and HEC1A endometrial cancer cell lines" CANCER CHEMOTHERAPY AND PHAR- MACOLOGY, SPRINGER, BERLIN, vol. 62, no. 3, 15 Nov. 2007, pages 483-489, XP819625528, ISSN: 1432-8843, disclose that the growth of existing cancer cells, when exposed to Mifepristone, is reduced. Hence, mifepristone (RU486), which has been disclosed more than 30 years ago, may become an important element in cancer treatment.

In [9], EP2210585A1, compositions with an antiprogestational action are described, which have the ability to prevent the intake of the composition by the patient in an abortive amount and avoid their misuse.

As detailed above, HCG fulfils important functions in the initial phase of human life but is no longer needed at a later stage. Cells need to be able to switch genes ON and OFF individually, e.g. in order to coordinate cohabitation with neighbour cells or to ensure that hormones required for specific functions are present or not. After HCG has fulfilled its purpose, the gene responsible for HCG production is switched OFF and the related nuclear receptors are no longer activated and transcription is ceased.

Mechanisms of action of nuclear receptors are described in [10], Aranda et al., "Nuclear Hormone Receptors and Gene Expression", PHYSIOLOGICAL REVIEWS, Vol. 81, No. 3, July 2001. For example, a lipophilic hormone may diffuse through the membrane of a cell to the cytosol. Once in the cytosol, the hormone binds to its cytosolic receptor, causing the release of an inhibitory protein from the receptor. The activated receptor then diffuses into the nucleus. In the nucleus, the receptor-hormone complex binds to the enhancer regions of hormone-regulated genes and transcription of the genes is stimulated, i.e. the gene is switched on.

While the function of HCG during the initial part of the embryonic phase is rather well known, potential effects of HCG in the post embryonic phase were not explored, as well.

In [11], M. J. Duffy and P. McGing, "Guidelines for the Use of Tumour Markers", Scientific Committee of the Association of Clinical Biochemists in Ireland (ACBI), 3$^{rd}$ Edition, April 2005, HCG is known as a Tumour Marker, which occurs in elevated levels in the event that a patient suffers from malignancies such as different kind of tumours. HCG is therefore used as an indicator for a malignancy.

It seems that in extremely seldom cases, about 1 in $10^{27}$, a gene in an adult cell required for hormone production, which should be switched OFF, is accidentally switched ON and the related hormone is produced. However, this accidental status change of the cell is not without reason or cause.

It is known that a cell can adapt to external conditions. Such adaptations are typically reversible changes in the number, size, phenotype, metabolic activity, or functions of cells in response to changes in their environment. Physiologic adaptations usually represent responses of cells to normal stimulation by hormones or endogenous chemical mediators. Pathologic adaptations are responses for example to stress that allow cells to modulate their structure and function and thus escape injury. Such adaptations can take several distinct forms.

In [12], Thomas Yuill, "Cellular adaptation to toxicity", National Library of Medicine, October 2006, it is described that adaptive changes often result in cells or organs that cannot function normally. This imperfect adaptation is a pathological change.

Hence, depending on environmental conditions and physiological and psychological influences or a mixture thereof to a human body, the cell system may be stressed and weakened and cells that suffer from pathological changes are prone to malfunction. Such an occurrence may be compared to an apparently inexplicable street accident, in which the driver has possibly actuated the accelerator pedal instead of the brake pedal. In such cases the driver has also been under the influence of psychological or environmental disturbances, which are more critical if the driver suffers from a weakness or illness at the same time. Similarly, a cell in a pathological state appears to act paradoxically at first sight. However, unfortunately, unlike the car driver, the cell will not encounter an adequate response to the malfunction but will remain under the impression that the selected state, with the undesirable gene function switched ON, is correct.

Hence, since some people will always be exposed to conditions, in which extensive cell adaptations over a longer period of time occur, e.g. by consumption of unhealthy nutrition, lack of physical exercises or disturbing influences, such as stress or unclean air, diseases will always occur that have the origin in the pathological state of cells located in a part of the human body.

In [13], Laurence A Cole, "hCG, the wonder of today's science" Reproductive Biology and Endocrinology 2012, http://www.rbej.com/content/10/1/24, it is stated that cancers start out as transformed cells driven by an HCG-independent process. Only after the cancer progresses and becomes advanced it would become able to express the HCG β-subunit gene and make HCG free β-subunit. The HCG free β-subunit driven TGFβ antagonism mechanism then would take over control of the cancer, as indicated by vaccine studies, and would reach complete control of the advanced disease.

SUMMARY OF THE INVENTION

Based on the foregoing, the primary object of the present invention is providing a composition or a group of compositions for inhibiting the occurrence of intra-cellular disorders in post natal or adult human organs, particularly cellular disorders in stressed cells that result in autocrine HCG-production.

Cells, particularly stressed cells, which are exposed to damaging influences shall be immunised against pathological cell behaviour and irritating signalling.

More particular, the invention is based on the object of preventing cell disorders that are caused and supported by the occurrence of autocrine HCG production in post-natal or adult cells and that lead to carcinogenesis.

Further, the composition shall be used for treatment of pathological cells and for inhibiting cell disorders causing diseases such as a deregulation of the immune defence system, reduced efficiency and effect or accuracy of DNA repair and impairment and foremost disturbances of the apoptosis function.

It is another object of the invention to provide such a composition or a group of compositions at comparatively low cost, with high efficiency and free of undesirable side-effects.

The above and other objects of the present invention are achieved with a composition according to claim 1 and a group of compositions according to claim 11.

As stated above, in the event that a gene that is required for HCG-production and that is present in a disturbed or stressed adult cell is accidentally switched ON due to a cell weakness or incorrect signalling, then autocrine production of HCG will start. According to the invention it has been found that autocrine production of HCG is not only the result but also the deciding cause of carcinogenesis.

In contradiction to the disclosure of [13], applicant has discovered that the development of malignant cancer in otherwise healthy adult cells starts by abnormal autocrine HCG-production that is only normal in early embryonic cell state. In other words, start of autocrine HCG-production can lead to carcinogenesis.

Tests in cell cultures show that nascent HCG from early embryonic states of mamifers, promotes cancerous cell growth. If the fresh cells have been given the equivalent of 0.5 mg per kg of a competitively binding progesterone antagonist, the above-mentioned doping with HCG did not result in cancerous cell growth.

By accidentally started autocrine HCG-production, the process of programmed cell death (PCD), apoptosis, is impaired. Since apoptosis is a critical maintenance function of the cell system that causes the death and safe removal of more than 50 billion deficient cells each day, even partial and local disturbances of the apoptosis-function are undesirable. While HCG is contributing to the condition required for the generation of life, it has been found harmful for the important process of the destruction of undesirable cell life, for which proliferation should be inhibited.

Besides a deregulation of the apoptosis function, autocrine HCG production will lead to impairment of the immune defence system, to hormonal disorders and reduced efficiency, effect or accuracy of the DNA repair mechanism of the cell. In adult cells, HCG molecules resulting from autocrine production facilitate activities of endogenous and of exogenous agents that cause DNA damages, which over years, due to disturbances of the apoptosis function, can increase and then can be the origin of a variety of diseases in the human body after many years.

The real possibility that a gene of an adult cell accidentally, but not without cause, reverts partially into an early embryonic state has not yet been considered seriously. This explains why no attempts to counteract such an effect have been explored.

Under real life conditions, an eventual and very rare accidental start of autocrine HCG-production in an adult human cell needs several years to eventually develop a detectable disease, for which HCG would be used as a suitable indicator.

Possibly an autocrine HCG producing cell, that is not jet detectable, can under some conditions, pervert neighbouring cells, thereby spreading and accelerating the propagation of the abnormal functioning of its gene.

DESCRIPTION OF THE INVENTION

Hence, a pharmaceutical composition or a group of such compositions is provided that is applied or applicable routinely by the user before cancer is detectable and before a cancer treatment is prescribed and corresponding medicaments are applied in high doses normally causing severe discomfort to the patient.

More precisely, the invention is a pre-emptive measure inhibiting the start of carcinogenesis by disabling a fundamental requirement of the process of carcinogenesis, namely autocrine HCG production.

Hence, the present invention is targeting the prevention of autocrine HCG production, for which an HCG antagonist or a substance with similar effect is used.

In [13], five unique variants of HCG molecules are described, each having identical amino acid sequence, produced by different cells and having independent functions. These are HCG, sulfated HCG, hyperglycosylated HCG, HCG free β-subunit and hyperglycosylated HCG free β-subunit. It is further stated that based on the vaccine studies it has been concluded, that development of a human high affinity HCG β-subunit antibody may be a future answer to human cancer treatment. At the extraordinarily mature state of the actual Endocrinology research and activity it has been a particular surprise to discover that the long known competitively binding progesterone antagonist is also able to antagonise the five variants of HCG molecules. Up to now, progesterone antagonists have been used mainly to avoid or terminate an early pregnancy. Several studies further indicate growth arrest of cancer cells in vitro and in vivo as mentioned above.

It could be shown, that surprisingly even a very low amount of a competitively binding progesterone antagonist as active agent is able to inhibit unwanted autocrine HCG production in adult cells, thus eliminating the risk of potential damage caused by this unwanted process.

Extrapolations of in vitro experiments indicate that already 0.1 mg to 2 mg per kg body weight and per year, preferably 0.5 mg to 1 mg per kg body weight and per year of the active agent are sufficient. However, as detailed below the dosage can be up to a factor 5 higher and can thus range between 0.1 mg to 10 mg per kg body weight and per year.

It has thus been a surprise to realize, that a progesterone antagonist is able to counteract and inhibit the autocrine HCG production of an adult cell.

The invention comprises therefore two significant steps. In the first step an important cause of oncogenesis, namely autocrine HCG production, as well as a solution for its suppression has been found, namely the application of HCG antagonists. In a second step it has been found that extremely small amounts of a competitively binding progesterone antagonist are suitable for antagonising the receptors, i.e. occupying the receptors with an antagonist, within the cells that produce native HCG as similarly produced by the Zygote. Hence, the progesterone antagonist, which is available on the market at comparatively low cost and which is used for inducing an abortion, is used as a substituent for an HCG-antagonist, which could be applied as well, but would be more costly since there has not yet been a large field of application.

Preferably the composition is applied with low volumes in intervals. Since the composition is applied for preventive purposes the required concentration is very low. A time spacing of approximately 3 to 24 months, preferably approximately 6 months, between applications showed good results in preliminary testing.

It is however recommended to administer a higher dose of the composition after a number of intervals. E.g., lower doses are applied at three months intervals while every eighteenth month a dosage is applied that is higher compared to the normal monthly dose by a factor in the range between 1.25 and 5. This factor is typically dependent of the amount of the monthly dose and the region of application. E.g., if the dosage is in the range of 0.1 mg to 0.5 mg per kg body weight and per year, then the maximum multiplication factor can be taken.

The active agent is preferably combined with at least one pharmaceutically acceptable carrier medium or excipient in order to improve the transport of the molecules of the active agent into the cytosol of the cells. The weight ratio of the active agent to the at least one carrier substance is preferably in the range between 1:10 and 1:250, most preferably at 1:33. The ratio is preferably selected according to the frequency of application. In the event that an application is made once a year, then a higher density in the range of 1:10 to 1:33 is seleceted.

Hence, the invention provides a pharmaceutical composition for use as medicament that inhibits autocrine Human Chorionic Gonadotropin (HCG) production in adult human cells, the composition comprising at least one pharmaceutically acceptable carrier medium and an active agent that is a competitively binding progesterone antagonist binding to steroid receptors of human cells, wherein the composition is provided in units designed for the monthly, semi-annual or annual application of the active agent in annual dosages in the range between 0.1 mg to 10.0 mg per kg of person/body-weight, preferably 0.5 mg to 3.0 mg per kg of person/body-weight.

The pharmaceutical composition according to claim 1, wherein the composition is provided
 a) in units for regular monthly consumption with each unit comprising an amount of the active agent in the range between 1 mg to 55 mg; or
 b) in units for regular semi-annual consumption with each unit comprising an amount of the active agent in the range between 10 mg to 500 mg; or
 c) in units for regular annual consumption with each unit comprising an amount of the active agent in the range between 25 mg to 1250 mg.

Preferably, the active agent is RU486 or RU534 or a mixture thereof. RU486 and RU534 are produced nowadays in large quantities and are therefore available at low cost. Further, with RU486 and RU534 the target of preventing autocrine HCG-production is successfully achieved, wherefore RU486 and RU534 are preferred substances for the inventive compositions.

It has been found that compositions are advantageously applicable that have been developed for contraceptive purposes such as the compounds disclosed in [3], U.S. Pat. No. 6,608,074B2 and [4], U.S. Pat. No. 6,316,432B1, which documents are herewith enclosed by reference. Suitable progesterone antagonists are for example:
 a) 11β-[4-N,N-(dimethylamino)phenyl]-17β-hydroxy-17α-propinyl-estra-4,9-dien-3-one, (RU486 or Mifepristone);
 b) 11β[(4-N,N-Dimethylamino)-phenyl]-17β-hydroxy-17α-propinyl-4,9(10)-estradien-3-one;
 c) 11β-[(4-N,N-dimethylamino)-phenyl]-17β-hydroxy-18-methyl-17α-propinyl-4,9(10)-estradien-3-one;
 d) 11β-(4-N,N-dimethylamino)-phenyl]-17aβ-hydroxy-17aα-propinyl-D-homo-4,9(10),16-estratrien-3-one;
 e) 11β-p-methoxyphenyl-17β-hydroxy-17α-ethinyl-4,9(10)-estradien-3-one;
 f) 11β-(4-acetylphenyl)-17β-hydroxy-17α-(prop-1-inyl)-4,9(10)-estradien-3-one;
 g) 11β-(4-Dimethylaminophenyl)-17α-hydroxy-17β-(3-hydroxypropy 1)-13α-methyl-4,9-gonadien-3-one;
 h) 11β-(4-acetylphenyl)-17β-hydroxy-17α-(3-hydroxyprop-1-enyl)-4,9(10)-estradien-3-one;
 i) 11β,19-[4-(cyanophenyl)-o-phenylene]-17β-hydroxy-17α-(3-hydroxyprop-1(Z)-enyl)-4-androsten-3-one;
 j) 11β,19-[4-(3-pyridinyl)-o-phenylene]-17β-hydroxy-17α-(3-hydroxyprop-1(Z)-enyl)-4-androsten-3-one; or
 k) 11β-[(4-N,N-dimethylamino)-phenyl]-17α-hydroxy-17β-(3-hydroxypropyl)-13α-methyl-4,9(10)-gondien-3-one
 l) Aglepristone (RU534).

The first compound is RU486 or Mifepristone, which can be used as active agent as well as substituents thereof.

The last compound is RU534 or Aglepristone is known from [14], F. Fieni et. al., "Mid-pregnancy termination in bitches with an antiprogestin: aglepristone (RU534)", published in "Advances in dog, cat and exotic carnivore reproduction", Oslo 2000.

The annual dosage of the composition, applied annually, semi-annually or monthly, is selected in the range between 0.1 mg to 2.0 mg per kg of person/body-weight, preferably 0.5 mg to 1.0 mg per kg of person/body-weight. The higher dosage being recommended for males and post-menopausal women Still further, the dosage is preferably adapted in accordance with environmental, habitual and genealogical considerations. In the event that the patient is exposed to stress and/or a genealogical handicap, then the dosage is preferably increased by a factor in the range of 2 to 5. Thus, the dosage and consequently the costs and efforts for the application can be optimised and kept extremely low, while the benefit is substantial.

For males and females above the age of 45 the above specified values of the dosage of application can be elevated by the factor 2-5.

According to the invention the absorption of the active agent is improved if a pharmaceutically acceptable first carrier medium is combined with the active agent that facilitates the transport of the molecules of the active agent into the cytosol of the cells.

Good results are achieved if the first carrier medium is a carrier protein, a cell penetrating peptide, a polar aprotic solvent such as Dimethyl sulfoxide (DMSO), a lipid, an alcohol, a permease, a liposome, a sulfur containing compound or a mixture thereof.

A safe and controllable application of the active agent is obtained, if a second pharmaceutically acceptable carrier medium is added to the composition. This second carrier is for example a liquid carrier, if the active agent shall be injected, a gelatine for sublingual application, a suppository for rectal application, a cream, spray or oil for mucosal or transdermal application, or syrup or a substance for producing pills or capsules for oral application.

For the treatment of an aggravated deficiency of the epithelium, carrier products, as creams, spray, suppository, transdermal patches can be useful to facilitate applications comprising 1 w %/W to 10 w %/W, preferably 2 w %/W to 5 w %/W of the active agent and the at least one carrier.

Hence, inhibiting autocrine HCG-production can be performed with low dosages that exhibit no side effects. Further, costs are extremely low even for general preventive application in the public. Potential risks are avoided or significantly reduced, which could lead to high healing costs and suffering of the patients.

In order to increase the impact of the active agent on the organelles of the adult cells, the second carrier medium can be a vitamin product or a multivitamin product available in liquid form or solid form, as sold in pharmacies. Such products are preferably combined with trace elements, such as Selenium, Zink, Phosphor and Copper. Such vitamin products or multivitamin products preferably contain vitamins B, particularly B17, C and D.

In order to further support intra-cellular functions, regulation and optimal enzyme production, the composition further preferably comprises at least
 a) one agent for causing reduction of endogenous glycation, such as Carnosine, Luteolin, Benfontiamine, Pyridoxal-5'-phosphate, or coenzyme Q10; and/or
 b) one antioxidant and components stimulating intracellular functions, such as L-cysteine, Resveratrol, Quercetin-dihydrate, DHEA, Green-tea, Curcumin extracts from Gynostemma pentaphyllum, or Cinnamon; and/or c) one agent supporting enhanced ATP production, such as phyto-therapeutic substances as Shilajit, Vinblastine, Saw-palmetto extract, Artimisia-annua, Methyl-jasmonate, Ascorbic-acid, Ginseng and the like.

Preferably a group of at least a first and a second composition is provided that comprise different carrier media, typically different second carrier media so that a are applicable in different parts of the body for forwarding the active agent via different pathways to a predetermined application zone.

Preferably the first composition, which is provided with a first concentration of the active agent, and the second composition, which is provided with a second concentration of the active agent, are adapted to one another in such a way that the desired amount of active agent is delivered to the field of application or target zone, while the concentrations of the active agent along the related pathways do not exceed specified values. Hence, the first and second composition, which are applied at different points of application, supplement or complement one another in order to obtain the desired concentration of the active agent at the target zone. Points of application may be the skin or the mouth of the user, while the common target zone may be a specific organ of the user. On both pathways the concentration of the active agent is comparably low while at the target point the desired concentration is reached. Since the applications of the different compositions are typically different, at least the second carrier media of these compositions are selected accordingly.

A highly effective preventive treatment of epithelial cells or a treatment of advanced epithelial cell defects for example is obtained, if two or more inventive compositions are administered concomitantly, topically and parenterally. Thereby, the inventive treatment occurs simultaneously from the inner side, i.e. the region of the blood vessels, and from the outer or topical side. Positive results can be obtained by this inventive 'bilateral' application of the active agent after a comparably short duration of application.

Hence, with an inventive group of compositions, on the one hand, concentrations of the active agent along the different pathways in the human body can be kept low, while at the same time the effect of the preventive treatment or the recovery of a treated human organ can be improved significantly.

For the application onto an epithelial area, a supporting carrier or medium for the inventive composition is preferably adapted or optimized accordingly. For example, for the treatment of epithelial problems in the colon, the second carrier may be a suppository. For skin problems, creams, lotions, gels, oils, sprays, patches, and the like, adapted for topical or transdermal application, are the preferred choice. For the treatment of old age Type 1 Diabetes or bucal-cavity problems, oral or sublingual application is an alternative, and for problems in the lung, a spray to be inhaled is a good carrier for the active agent. For gastro-intestinal problems, the composition is preferably administered in a (XR) slow release formula.

In a first embodiment of the invention the second carrier medium of the first composition is a medium for oral, inhalatory or sublingual application and the second carrier medium of the second composition is a medium for transdermal or mucosal application.

In a second embodiment the second carrier medium of the first composition is a medium for oral, inhalatory or sublingual application and the second carrier medium of the second composition is a liquid determined for inoculation or a suppository particularly for rectal application.

In a further embodiment the second carrier medium of the first composition is a liquid determined for inoculation and the second carrier medium of the second composition is a suppository or a medium for mucosal application. Further combinations can be selected as desired.

For females, concentrations internally applied in the region of the lower abdomen are preferably lower by a factor in the range from 2 to 5 compared to a composition applied e.g. transdermally in the in the breast region.

Consequently, the invention allows to 1 advantageously apply the inventive composition adapted to the sex, the weight, the age, the genealogy, and the physical and psychological condition of the patient without inducing side effects.

REFERENCES

[1] Marie Tsampalas et al., "Human chorionic gonadotropin: A hormone with immunological and angiogenic properties", 2010 Elsevier Ireland Ltd.
[2] B. Maria et al., "Termination of early pregnancy by a single dose of mifepristone (RU486), a progesterone antagonist", European Journal of Obstetrics & Gynecology and Reproductive Biology, (1988, Jul. 1), vol. 28, no. 3, pages 249-255
[3] U.S. Pat. No. 6,608,074B2
[4] U.S. Pat. No. 6,316,432B1
[5] "New Zealand Data Sheet of Mifegyne", 3 Jul. 2013, XP855181287
[6] Wu et al: "Effects of mifepristone on the proliferation, apoptosis, and taxol sensitivity of drug-resistant human ovarian cancer cells", 2012, XP002728256, http://en-.cnki.com.cn/Article_en/CJFDTOTAL-ZGAZ201202009.htm
[7] CHELSEA R TIESZEN ET AL: "Antiprogestin mifepristone inhibits the growth of cancer cells of reproductive and non-reproductive origin regardless of progesterone receptor expression", BMC CANCER, BIOMED CENTRAL, LONDON, vol. 11, no. 1, 27 May 2011, page 287, XP021099346, ISSN: 1471-2487, DOI: 10.1186/1471-2407-11-207
[8] MARISA A NAVO ET AL: "In vitro evaluation of the growth inhibition and apoptosis effect of mifepristone (RU486) in human Ishikawa and HEC1A endometrial cancer cell lines" CANCER CHEMOTHERAPY AND PHARMACOLOGY, SPRINGER, BERLIN, vol. 62, no. 3, 15 Nov. 2007, pages 483-489, XP819625528, ISSN: 1432-8843
[9] EP2210585A1,
[10] Aranda et al., Nuclear Hormone Receptors and Gene Expression, PHYSIOLOGICAL REVIEWS, Vol. 81, No. 3, July 2001
[11] M. J. Duffy and P. McGing, Guidelines for the Use of Tumour Markers, Scientific Committee of the Association of Clinical Biochemists in Ireland (ACBI), $3^{rd}$ Edition, April 2005
[12] Thomas Yuill, Cellular adaptation to toxicity, National Library of Medicine, October 2006
[13] Laurence A Cole, "hCG, the wonder of today's science" Reproductive Biology and Endocrinology 2012, http://www.rbej.com/content/10/1/24
[14] F. Fieni et. al., "Mid-pregnancy termination in bitches with an antiprogestin: aglepristone (RU534)", Laborarory of Biotechnology and Pathology of Reproduction, National Vererinary School, Nantes, France; published in "Advances in dog, cat and exotic carnivore reproduction", Oslo 2000

The invention claimed is:

1. A method of inhibiting autocrine Human Chorionic Gonadotropin (HCG) production by human cells, comprising:
   administering a pharmaceutical composition to a postnatal female or adult female human, prior to development of a detectable disorder or disease, in an amount effective to achieve an annual total active agent dosage of from 0.1 mg to 1.0 mg per kg of body weight of the human, wherein:
   the pharmaceutical composition comprises a pharmaceutically acceptable carrier and an active agent that is a competitively binding progesterone antagonist that binds to one or more steroid receptors of human cells; and
   the pharmaceutical composition is administered from every 1 to 12 months.

2. The method of claim 1, wherein the cells are prone to autocrine HCG production due to being in a disturbed or stressed state.

3. The method of claim 1, wherein the method is performed to inhibit an intra-cellular disorder that would otherwise result in autocrine HCG production.

4. The method of claim 1, wherein the active agent is RU486 or RU534.

5. The method of claim 1, wherein the method is performed to inhibit the start of carcinogenesis.

6. The method of claim 1, wherein the pharmaceutical composition is administered monthly, semi-annually, or annually.

7. The method of claim 1, wherein the active agent is selected from the group consisting of:
   11β[(4-N,N-dimethylamino)-phenyl]-17β-hydroxy-17α-propinyl-4,9(10)-estradien-3-one;
   11β-[(4-N,N-dimethylamino)-phenyl]-17β-hydroxy-18-methyl-17α-propinyl-4,9(10)-estradien-3-one;
   11β-(4-N,N-dimethylamino)-phenyl]-17aβ-hydroxy-17aα-propinyl-D-homo-4,9(10),16-estratrien-3-one;
   11β-p-methoxyphenyl-17β-hydroxy-17α-ethinyl-4,9(10)-estradien-3-one;
   11β-(4-acetylphenyl)-17β-hydroxy-17α-(prop-1-inyl)-4,9(10)-estradien-3-one;
   11β-(4-dimethylaminophenyl)-17α-hydroxy-17β-(3-hydroxypropyl)-13α-methyl-4,9-gonadien-3-one;
   11β-(4-acetylphenyl)-17β-hydroxy-17α-(3-hydroxyprop-1-enyl)-4,9(10)-estradien-3-one;
   11β,19-[4-(cyanophenyl)-o-phenylene]-17β-hydroxy-17α-(3-hydroxyprop-1(Z)-enyl)-4-androsten-3-one;
   11β,19-[4-(3-pyridinyl)-o-phenylene]-17β-hydroxy-17α-(3-hydroxyprop-1(Z)-enyl)-4-androsten-3-one; and
   11β-[(4-N,N-dimethylamino)-phenyl]-17α-hydroxy-17β-(3-hydroxypropyl)-13α-methyl-4,9(10)-gondien-3-one.

8. The method of claim 1, wherein the pharmaceutical composition comprises a first pharmaceutically acceptable carrier that supports the transport of the molecules of the active agent into the cytosol of the cells.

9. The method of claim 8, wherein the first carrier comprises a carrier protein, a cell-penetrating peptide, a polar aprotic solvent, a lipid, an alcohol, a permease, a liposome, a sulfur-containing compound, or a combination thereof.

10. The method of claim 8, wherein the pharmaceutical composition further comprises a second pharmaceutically acceptable carrier that is a liquid, a gelatine, a suppository, a cream, a spray, an oil, a syrup or a substance used for producing pills.

11. The method of claim 10, wherein the second carrier comprises a vitamin or multivitamin product.

12. The method of claim 10, wherein the second carrier comprises trace elements.

13. The method of claim 10, wherein the second carrier comprises at least one agent for reducing endogenous glycation, at least one antioxidant and components for stimulating intracellular functioning, or at least one agent for supporting enhanced ATP production.

14. The method of claim 1, wherein the pharmaceutical composition is administered by injection, sublingual administration, mucosal administration, transdermal administration, or oral administration.

15. The method of claim 1, wherein the weight ratio of the active agent to the carrier is from 1:10 to 1:250.

16. The method of claim 1, wherein:
   at least first and second pharmaceutical compositions are administered to the human in amounts effective to achieve the annual total active agent dosage of from 0.1 mg to 1.0 mg per kg of body weight of the human; and
   the first and second pharmaceutical compositions each comprise (i) the pharmaceutically acceptable carrier, and (ii) the competitively binding progesterone antagonist in different concentrations so as to complement one another in order to provide the annual total active agent dosage.

17. The method of claim 16, wherein the first and second pharmaceutical compositions each comprise at least a first and a second pharmaceutically acceptable carrier.

18. The method of claim 17, wherein the first carrier is a carrier that supports the transport of the molecules of the active agent into the cytosol of the cells.

19. The method of claim 18, wherein the first carrier comprises a carrier protein, a cell-penetrating peptide, a polar aprotic solvent, a lipid, an alcohol, a permease, a liposome, a sulfur-containing compound, or a combination thereof.

20. The method of claim 18, wherein the second carrier is a liquid, a gelatine, a suppository, a cream, a spray, an oil, a syrup or a substance used for producing pills.

21. The method of claim 16, wherein the first pharmaceutical composition is administered via epithelial blood vessels, and the second pharmaceutical composition is administered by application onto skin.

22. The method of claim 16, wherein the first pharmaceutical composition is administered by oral or sublingual administration, and the second pharmaceutical composition is administered by transdermal or mucosal administration.

23. The method of claim 16, wherein the first pharmaceutical composition is administered by injection, and the second pharmaceutical composition is administered by mucosal administration.

24. The method of claim 1, wherein the annual total active agent dosage is from 0.1 mg to 0.5 mg per kg of body weight of the human.

25. A method of inhibiting autocrine Human Chorionic Gonadotropin (HCG) production by human cells, comprising:
   administering a pharmaceutical composition to a postmenopausal female human, prior to development of a detectable disorder or disease, in an amount effective to achieve an annual total active agent dosage of from 0.1 mg to 10.0 mg per kg of body weight of the human, wherein:
   the pharmaceutical composition comprises a pharmaceutically acceptable carrier and an active agent that is a competitively binding progesterone antagonist that binds to one or more steroid receptors of human cells; and the pharmaceutical composition is administered from every 1 to 12 months.

26. The method of claim 25, wherein the pharmaceutical composition is administered monthly at a monthly active agent dosage of from 1 mg to 55 mg.

27. The method of claim 25, wherein the pharmaceutical composition is administered semi-annually at a semi-annual active agent dosage of from 10 mg to 500 mg.

28. The method of claim 25, wherein the pharmaceutical composition is administered annually at an annual active agent dosage of from 25 mg to 1250 mg.

* * * * *